United States Patent [19]

Johnston et al.

[11] 4,066,438
[45] Jan. 3, 1978

[54] SUBSTITUTED AMINODI- OR TRIHALOPYRIDINES AND METHOD OF USE

[75] Inventors: Howard Johnston, Walnut Creek, Calif.; Herman O. Senkbeil, Midland, Mich.

[73] Assignee: The Dow Chemical Company, Midland, Mich.

[21] Appl. No.: 676,035

[22] Filed: Apr. 12, 1976

Related U.S. Application Data

[63] Continuation-in-part of Ser. No. 571,151, April 24, 1975, abandoned, which is a continuation-in-part of Ser. No. 177,429, Sept. 2, 1971, abandoned, which is a continuation-in-part of Ser. No. 124,571, March 15, 1971, abandoned, which is a continuation-in-part of Ser. No. 40,389, May 25, 1970, abandoned.

[51] Int. Cl.² .................. C07D 213/61; A01N 9/22
[52] U.S. Cl. ........................... 71/94; 260/295 R; 260/295 AM; 260/294.8 G; 260/296 AE
[58] Field of Search ....... 260/296 R, 295 R, 295 AM, 260/294.8 G, 296 AE; 71/94

[56] References Cited

U.S. PATENT DOCUMENTS

| 3,317,542 | 5/1967 | Haszeldine et al. ............. 260/296 R |
| 3,838,159 | 9/1974 | Johnston ........................ 260/296 R |

FOREIGN PATENT DOCUMENTS

| 1,161,492 | 8/1969 | United Kingdom ............ 260/296 R |

*Primary Examiner*—Natalie Trousof
*Assistant Examiner*—Robert T. Bond

*Attorney, Agent, or Firm*—S. Preston Jones; C. Kenneth Bjork

[57] ABSTRACT

Novel compounds corresponding to the formula

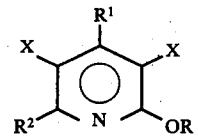

and the organic or inorganic acid addition salts thereof, wherein X represents chloro, bromo or fluoro; $R^1$ represents hydrogen, amino, loweralkylamino, arylamino, loweralkylamido or N-(loweralkyl)loweralkylamido; $R^2$ represents hydrogen, X, amino or loweralkylamino, with the proviso that one of $R^1$ or $R^2$ is always amino or loweralkylamino and the other of $R^1$ or $R^2$ is other than amino or loweralkylamino; R represents butyl, 2-hydroxypropyl, 4-hydroxybutyl, 6-hydroxyhexyl or the radical

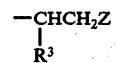

wherein Z represents amino, lower-alkylamino, phenylamino, hydroxy, loweralkoxy, aryloxy, 2-propenyl, hydroxyloweralkoxy, mercapto, loweralkylthio, loweralkanoyloxy or 2-haloloweralkanoyloxy and $R^3$ represents hydrogen or methyl and with the proviso that R is other than butyl when $R^2$ is X are prepared. These compounds are useful as herbicides and as active agents in compositions used as herbicides.

21 Claims, No Drawings

SUBSTITUTED AMINODI- OR TRIHALOPYRIDINES AND METHOD OF USE

CROSS-REFERENCE TO RELATED APPLICATION

This application is a continuation-in-part of application Ser. No. 571,151, filed Apr. 24, 1975, now abandoned, which in turn is a continuation-in-part of application Ser. No. 177,429, filed Sept. 2, 1971, now abandoned, which in turn is a continuation-in-part of application Ser. No. 124,571, filed Mar. 15, 1971, now abandoned, which is in turn a continuation-in-part of application Ser. No. 40,389, filed May 25, 1970, now abandoned.

DESCRIPTION OF THE PRIOR ART

Various substituted pyridine compounds are known in the prior art, for example, British Pat. No. 1,161,492 teaches 6-fluoro pyridine compounds of the formula

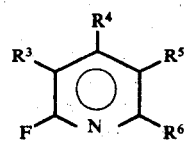

or a salt thereof, wherein $R^3$ and $R^5$ represent chloro or fluoro; and $R^4$ and $R^5$ represent chloro or fluoro or substituted or unsubstituted alkyl, alkenyl, alkoxy, aryl, arkaryl, aryloxy, hydroxy, carboxyl or a functional derivative thereof, acyl, acyloxy, mercapto, acylthio, sulpho, amino, hydrazino, amido, amidino, azido, ureido, carbamoyl, nitro, cyano or heterocyclic groups, provided that when $R^4$ is hydroxy, acyloxy, acylthio, mercapto or substituted mercapto, $R^6$ is not chloro or fluoro; and when $R^6$ is hydroxy, $R^4$ is not fluoro or chloro; however, no method of preparing the compound is taught. In addition, British Pat. No. 1,159,036 teaches fluoropyridine compounds of the formula

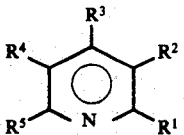

wherein one of $R^1$ and $R^2$ represent fluoro and the other represent amino or methoxy; $R^3$ represents amino or nitro; $R^4$ represents fluoro; $R^5$ represents fluoro or amino and amino only when $R^2$ represents amino. Specific compounds taught by this reference include 3-amino-2,5,6-trifluoro-4-nitropyridine, 2-amino-3,5,6-trifluoro-4-nitropyridine, 2,3,5-trifluoro-6-methoxy-4-nitropyridine and 4-amino-2,3,5-trifluoro-6-methoxypyridine.

SUMMARY OF THE INVENTION

The present invention is directed to novel compounds corresponding to the formula

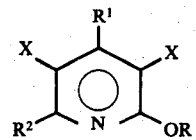

and the organic and inorganic acid addition salts thereof. In this and succeeding formulae X represents chloro, bromo or fluoro; $R^1$ represents hydrogen, amino, loweralkylamino, arylamino, loweralkylamido, or N-(loweralkyl)loweralkylamido; $R^2$ represents hydrogen, X, amino or loweralkylamino; with the proviso that one of $R^1$ or $R^2$ is always amino or loweralkylamino and the other of $R^1$ or $R^2$ is other than amino or loweralkylamino; R represents butyl, 2-hydroxypropyl, 4-hydroxybutyl, 6-hydroxyhexyl or the radical

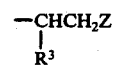

wherein Z represents amino, loweralkylamino, phenylamino, hydroxy, loweralkoxy, aryloxy, 2-propenyl, hydroxyloweralkoxy, mercapto, loweralkylthio, loweralkanoyloxy or 2-haloloweralkanoyloxy and $R^3$ represents hydrogen or methyl and with the proviso that R is other than butyl when $R^2$ is X.

In the present specification and claims the term "loweralkyl" is employed to designate a straight or branch alkyl radical containing from 1 to 6 carbon atoms.

The term "loweralkoxy" as employed in the present specification and claims designates either straight or branched chain alkoxy radicals containing from 1 to 6 carbon atoms.

The term "hydroxy loweralkoxy" as employed in the present specification and claims designates either straight or branched chain alkoxy radicals having a hydroxy group in a terminal position relative to the alkoxy oxygen and containing from 2 to 6 carbon atoms.

The term "aryloxy" as employed in the present specification and claims designates a member of the group consisting of phenyloxy, benzyloxy, phenylethoxy, phenylpropoxy and phenylbutoxy.

The term "loweralkylamino" as employed in the present specification and claims designates either straight or branched chain mono- or dialkylamino radicals containing from 1 to 4 carbon atoms.

The term "loweralkylamido" as employed in the present specification and claims designates either straight or branched chain monoalkylamido radicals containing from 2 to 4 carbon atoms.

The term "arylamino" as employed in the present specification and claims designates an aromatic amine from the group consisting of phenylamine, benzylamine, phenylethylamine, phenylpropylamine and phenylbutylamine.

The term "loweralkylthio" as employed in the present specification and claims designates either straight or branched chain alkylthio radicals containing from 1 to 4 carbon atoms.

The term "loweralkanoyloxy" as employed in the present specification and claims designates a straight chain alkanoyloxy radical containing from 2 to 4 carbon atoms.

The term "2-haloloweralkanoyloxy" as employed in the present specification and claims designates a straight chain alkanoyloxy radical containing from 2 to 4 carbon atoms and in addition containing from 1 to 3 chlorine or fluorine atoms attached to the alpha carbon, i.e., the carbon atom attached to the carbonyl group.

The phrase "organic or inorganic acid addition salt" as employed in the present specification and claims designates addition salts of the pyridine compounds with an acid such as hydrochloric acid, hydrobromic acid, hydroiodic acid, sulfuric acid, phosphoric acid, nitric acid, dichloroacetic acid, trichloroacetic acid and 2,2-dichloropropionic acid.

The present invention also is understood to encompass compounds wherein all the "X" substituents are the same as well as those wherein different halogens are present in the same compound.

The present invention is also directed to plant husbandry and the raising of crops and is concerned with an agronomical practice and composition for improving the emergence, seed germination, seedling growth and harvest of crop plants. This invention also relates to herbicidal compositions and to methods of inhibiting or controlling undesirable plant growth therewith in the presence of important economic crops.

The active compounds of the present invention are crystalline solids or oils which are slightly soluble in common organic solvents.

The substituted aminohalopyridines of the present invention are prepared by the reaction of an aminohalopyridine with an appropriate alcohol according to the following equation wherein R, $R_1$, $R_2$ and X have the significance previously given:

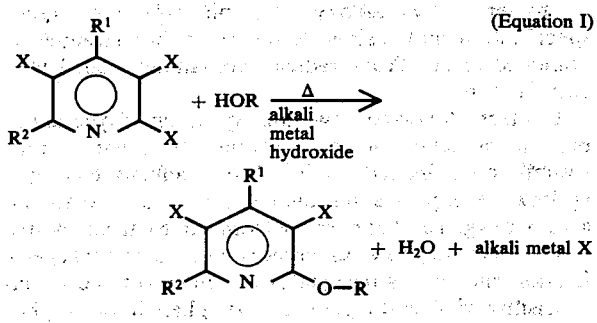
(Equation I)

The reaction is initiated by contacting the reactants together in the presence of a base such as, for example, sodium hydroxide, potassium hydroxide or lithium hydroxide at a temperature in the range of from about 100° C. to about 170° C., preferably at a temperature of about 150° C. The reaction consumes the reactants in stoichiometric proportions, i.e., one equivalent of the pyridine reactant per equivalent of the alcohol reactant. However, due to the nature of the ether formation, it is preferred that an excess of the alcohol reactant be employed. In some instances, it is desirable to carry out the reaction in an inert solvent such as, for example, dimethylsulfoxide, dimethylformamide or a polyglycol ether.

In carrying out the reaction, the base is usually first dissolved in a portion of the alcohol reactant and this mixture is added to a mixture of the pyridine and alcohol reactants. This reaction mixture is thereafter heated, with agitation, to a reaction temperature of between about 120° C. to about 160° C. and maintained at this temperature and in a state of agitation for about 1 to 4 hours, until the reaction is complete. The reaction mixture is cooled and usually added to water and the product recovered by extraction with a suitable solvent, such as, for example, methylene chloride, cloroform or benzene. If desired, the product can be purified by conventional techniques such as, for example, solvent washing and/or recrystallization from a solvent such as hexane, nitromethane, hexane-chloroform, benzene and the like.

The organic and inorganic acid salts are prepared by dissolving the appropriate substituted aminohalopyridine compound in a dilute solution of the desired organic or inorganic acid. This addition usually is carried out at room temperature and atmospheric pressure and with continuous agitation. The so-formed salts are insoluble in the acid solution and readily precipitate from the acid solution. The product is usually recovered by filtration and if desired, can be further purified by conventional techniques as hereinabove set forth.

The compounds wherein Z is loweralkanoyloxy or 2-haloloweralkanoyloxy are prepared by reacting an appropriate acyl chloride with the appropriate 2-alkanol amino halopyridine. In carrying out this reaction, the pyridine compound is dissolved in pyridine and brought to a temperature of about 0° C. to 100° C. and the acyl chloride is slowly added thereto, with agitation. This reaction mixture is maintained under constant agitation for about 1 hour, added to water and the product extracted therefrom with a solvent, such as, methylene chloride, benzene or chloroform. The extract is thereafter washed with water, dried and the solvent removed by conventional techniques, such as evaporation under reduced pressure. If desired, the product can be further purified by conventional techniques such as those hereinbefore set forth. Representative acyl chlorides include, for example, acetyl chloride, propionyl chloride, butyryl chloride, chloroacetyl chloride, dichloroacetyl chloride, 2,2-dichloropropionyl chloride, 2-chlorobutyryl chloride and 2,2-dichlorobutyryl chloride.

DESCRIPTION OF THE PREFERRED EMBODIMENTS

The following examples illustrate the present invention and the manner by which it can be practiced but, as such, should not be construed as limitations upon the overall scope of the same.

EXAMPLE I

4-Amino-3,5-dichloro-2-(2-hydroxyethoxy)pyridine

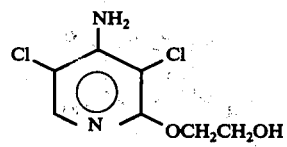

A mixture of 200 grams (1.1 mole) of 4-amino-2,3,5-trichloropyridine in 500 milliliters of ethylene glycol was heated at 108° C., with agitation, until a solution was obtained. To this solution was added over a 20-minute period, while the temperature was raised to 123° C., a solution of 70 grams (1.25 mole) of potassium hydroxide dissolved in 300 milliliters of ethylene glycol. The temperature was raised to 150°–151° C. and agitation was maintained for 2 hours. The reaction mixture was cooled and filtered under reduced pressure. The filtrate was diluted with 1500 milliliters of cold water and extracted with methylene chloride. The solvent was removed by evaporation under reduced pressure. The liquid residue which remained was crystallized from hexane and dissolved in hot chloroform. The solution was cooled and the 4-amino-3,5-dichloro-2-(2-hydroxyethoxy)pyridine product was recovered by filtration under reduced pressure. The purified product was recovered in a yield of 75 grams which melted at 77.5°–81° C.

EXAMPLE II

4-Amino-3,5-dichloro-2-(2-hydroxyethoxy)pyridine, hydrochloride

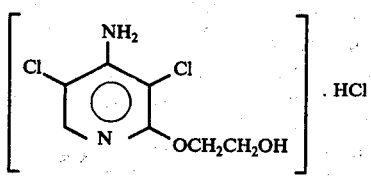

Ten grams of 4-amino-3,5-dichloro-2-(2-hydroxyethoxy)pyridine, prepared in Example I, was dissolved in 50 milliliters of 5 Normal hydrochloric acid, at ambient temperature, with agitation. The solid which precipitated was recovered by filtration under reduced pressure and dried. The 4-amino-3,5-dichloro-2-(2-hydroxyethoxy)pyridine, hydrochloride product was recovered in a yield of 95 percent of theoretical and melted at 169° C. to 170° C.

EXAMPLE III

4-Amino-2-(2-aminoethoxy)-3,5-dichloropyridine

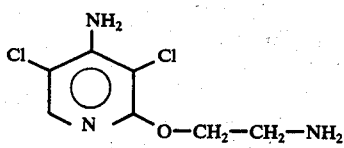

A mixture containing 21.4 grams (0.35 mole) of 2-aminoethanol, 50 milliliters of dimethylsulfoxide and 20 grams (0.36 mole) of potassium hydroxide was heated at 110° C. until all of the potassium hydroxide was reacted. The solution was added to a mixture containing 69 grams (0.35 mole) of 4-amino-2,3,5-trichloropyridine dissolved in 200 milliliters of dimethylsulfoxide. The mixture was heated for 1½ hours at 138° C. to 150° C. under agitation and thereafter quenched by pouring into ice water. The solid which precipitated was recovered by filtration under reduced pressure, dried and recrystallized from a mixture of hexane and chloroform. The solid was dissolved in 100 milliliters of dimethylsulfoxide and mixed with a solution composed of 21.4 grams (0.35 mole) of 2-aminoethanol and 20 grams (0.36 mole) of potassium hydroxide dissolved in 50 milliliters of dimethylsulfoxide. This mixture was heated for 2 hours at 150° C., cooled by quenching with ice water to precipitate the product as a solid which was recovered by filtration under reduced pressure. This product was distilled under azeotropic conditions with benzene to remove water from the 4-amino-2-(2-aminoethoxy)-3,5-dichloropyridine product which has a melting point of 115°–116.5° C.

EXAMPLE IV

4-Amino-3,5-dichloro-2-(2-methoxyethoxy)pyridine

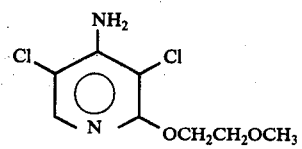

A solution of 16.5 grams (0.25 mole) of 86 percent potassium hydroxide dissolved in 100 milliliters of 2-methoxyethanol was added to a mixture of 49.5 grams (0.25 mole) of 4-amino-2,3,5-trichloropyridine in 150 milliliters of 2-methoxyethanol. The mixture was heated, with agitation, to 118° C. and held between 118°–120° C. for 3½ hours. The reaction mixture was cooled to 75° C. and filtered under reduced pressure to remove the insoluble solids. The excess 2-methoxyethanol was evaporated off under reduced pressure and the liquid residue remaining was crystallized from hexane. The 4-amino-3,5-dichloro-2-(2-methoxyethoxy)pyridine product was recovered by filtration under reduced pressure, and obtained in a yield of 57 grams melting at 92°–93.5° C.

EXAMPLE V

4-Amino-3,5-dichloro-2-(2-acetoxyethoxy)pyridine

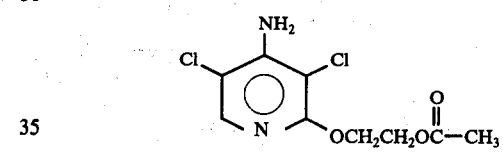

To a solution of 22.3 grams (0.1 mole) of 4-amino-3,5-dichloro-2-(2-hydroxyethoxy)pyridine (prepared by the method of Example I) dissolved in 150 milliliters of pyridine was added dropwise, with agitation, 8.7 grams (0.11 mole) of acetylchloride. The mixture was brought to reflux (~100° C.) and held at this temperature for 1 hour. The mixture was cooled to room temperature and poured into water. The oil which separated was extracted with methylene chloride, washed with 200 milliliters of water and dried over potassium carbonate. The solvent was evaporated under reduced pressure and the 4-amino-3,5-dichloro-2-(2-acetoxyethoxy)pyridine product was recovered by recrystallization from hexane. The product was recovered in a yield of 13.7 grams which melts at 76°–77° C.

The following compounds of the present invention are prepared in accordance with the methods hereinabove set forth.

3,5-dichloro-2-(2-hydroxyethoxy)-4-methylamino pyridine; melting at 53°–55° C.
3,5-dichloro-2-(2-hydroxyethoxy)-4-n-propylamino pyridine; having a molecular weight of 265.02.
3,5-dichloro-2-(2-hydroxyethoxy)-2-n-propylamino pyridine; sulfuric acid salt; having a molecular weight of 363.09.
3,5,6-trichloro-2-(2-hydroxyethoxy)-2-methylamino pyridine; having a melting point of 65°–67° C.
6-amino-3,5-dichloro-2-(2-hydroxyethoxy)pyridine; melting at 68°–69° C.
6-amino-3,5-dichloro-2-(2-hydroxyethoxy)pyridine, hydroiodide; having a molecular weight of 350.90.

4-amino-3,5,6-trichloro-2-(2-hydroxy-1-methylethoxy)-pyridine; having a molecular weight of 259.45.

4-amino-3,5-dichloro-2-(2-hydroxy-1-methylethoxy)-pyridine; boiling at 94°–102° C. at 2.0 microns of mercury.

4-anilino-3,5-dichloro-6-fluoro-2-(2-hydroxy-1-methylethoxy)pyridine; having a molecular weight of 331.06.

4-amino-3,5-dichloro-2-[2-(benzyloxy)ethoxy]pyridine; melting at 44.5°–46° C.

4-acetamido-3,5-dichloro-2-(2-hydroxyethoxy)pyridine; having a molecular weight of 265.01.

4-amino-3,5-dichloro-2-[2-(2-hydroxyethoxy)ethoxy]-pyridine; melting at 100°–101° C.

6-amino-3,5-dichloro-2-(2-trichloroacetoxy-1-methylethoxy)pyridine; having a molecular weight of 382.40.

4-amino-3,5-dibromo-2-(2-hydroxyethoxy)pyridine; having a molecular weight of 311.96.

6-amino-3,5-dichloro-2-(2-chloroacetoxyethoxy)-pyridine; having a molecular weight of 299.47.

4-amino-3,5,6-trifluoro-2-(2-hydroxyethoxy)pyridine; having a melting point of 123°–125° C.

3,5-difluoro-4-dimethylamino-2-(2-hydroxyethoxy)-pyridine; having a molecular weight of 218.09.

3,5-difluoro-4-dimethylamino-2-(2-hydroxyethoxy)-pyridine, sulfuric acid salt; having a molecular weight of 316.16.

6-amino-5-bromo-3-chloro-2-[2-(methylthio)ethoxy]-pyridine; having a molecular weight of 297.51.

4-amino-3,5-dichloro-2-(6-hydroxyhexoxy)pyridine; having a molecular weight of 289.03.

4-amino-3,5-dichloro-2-(6-hydroxyhexoxy)pyridine, dichloroacetic acid salt; having a molecular weight of 417.07.

3,5,6-trichloro-2-(2-hydroxyethoxy)-4-N-butylaminopyridine; having a molecular weight of 313.49.

4-(benzylamino)-3,5-dichloro-2-(2-hydroxyethoxy)-pyridine; having a molecular weight of 329.06.

3,5,6-trifluoro-2-[1-methyl-2-(4-phenylbutoxy)-ethoxy]-4-[(4-phenylbutyl)amino]pyridine; having a molecular weight of 486.28.

2-(2-anilinoethoxy)-3,5-dibromo-4-butyramido-6-fluoropyridine; having a molecular weight of 475.01.

4-[N-methylacetamido]-3,5-dichloro-2-fluoro-2-(2-hydroxyethoxy)pyridine; having a molecular weight of 281.02.

3,5-dichloro-2-(2-hydroxyethoxy)-6-dimethylamino pyridine; melting at 52°–53° C.

3,5-dichloro-2-[2-(2,2-dichlorobutyroyloxy)ethoxy]-6-dimethylamino pyridine; having a molecular weight of 389.97.

3,5-dichloro-2-(2-hydroxyethoxy)-4-n-propylamino pyridine, hydrobromide; having a molecular weight of 345.94.

3,5-dibromo-2-(2-butoxyethoxy)-6-methylamino pyridine; having a molecular weight of 381.96.

3,5-dibromo-4-methylamino-2-[2-dimethylamino)-1-methylethoxy]pyridine; having a molecular weight of 365.95.

4-amino-3,5-dichloro-2-[2-(2-propenoxy)ethoxy]-pyridine; melting at 41°–43° C.

4-amino-3,5-dichloro-2-[2-(methylthio)ethoxy]pyridine; melting at 100°–102° C.

3,5-dibromo-4-diethylamino-2-[2-(4-hydroxybutoxy)-1-methylethoxy]pyridine; having a molecular weight of 438.00.

4-amino-3,5-dichloro-6-fluoro-2-(2-hydroxyethoxy)-pyridine; having a melting point of 105°–106.5° C.

3,5-dibromo-4-diethylamino-2-[2-(butyroyloxy)-ethoxy]pyridine; having a molecular weight of 437.99.

6-butylamino-3,5-difluoro-2-(2-hydroxyethoxy)-pyridine; having a molecular weight of 247.11.

4-amino-3,5-dichloro-2-butoxy pyridine; boiling at 108°–112° C. at 0.2 millimeters of mercury.

4-amino-3,5-dichloro-2-(3-ethoxy-2-hydroxypropoxy)-pyridine; having a molecular weight of 281.02.

6-amino-3,5-difluoro-2-(2-mercaptoethoxy)pyridine; having a molecular weight of 190.14.

4-(N-butylbutyramido)-3,5,6-trichloro-2-(2-phenoxyethoxy)pyridine; having a molecular weight of 459.59.

4-amino-3,5-dichloro-2-(2-acetoxyethoxy)pyridine; having a melting point of 76°–77° C.

4-acetamido-3,5-dichloro-2-(2-hydroxyethoxy)-pyridine; having a molecular weight of 265.01.

4-acetamido-3,5-dichloro-2-(2-acetoxyethoxy)-pyridine, having a melting point of 131.2°–132° C.

6-amino-3,5-difluoro-2-(2-mercaptoethoxy)pyridine; trichloroacetic acid salt; having a molecular weight of 369.54.

4-amino-3,5,6-trichloro-2-(2-ethoxy-1-methylethoxy)-pyridine; having a molecular weight of 297.48.

4-amino-3,5-dichloro-2-(2-t-butoxyethoxy)pyridine; melting at 72.5°–76° C.

6-amino-3,5-dichloro-2-[2-(butylthio)-1-methylethoxy]-pyridine; having a molecular weight of 309.11.

4-dibutylamino-3,5-difluoro-2-(2-hydroxyethoxy)-pyridine; having a molecular weight of 299.15.

4-dibutylamino-3,5-difluoro-2-(2-hydroxyethoxy)-pyridine; 2,2-dichloropropionic acid salt; having a molecular weight of 442.10.

4-amino-3,5-dichloro-2-(4-hydroxybutoxy)pyridine; melting at 91°–92.5° C.

3,5-dichloro-4-dimethylamino-2-(2-hydroxyethoxy)-pyridine; boiling at 80° C. at 0.1 micron of mercury.

4-amino-3,5,6-trichloro-2-(2-hydroxyethoxy)pyridine; having a melting point of 88°–90° C.

In accordance with the present invention, it has been discovered that the substituted aminohalopyridines of the present invention are useful as herbicides. In accordance with this invention, a method for controlling or inhibiting the growth of undesirable plant species is provided which comprises applying to plants, plant parts or their habitat, an effective or growth inhibiting amount of at least one of the substituted aminohalopyridines as set forth hereinabove.

An outstanding feature of the present invention is the ability of the pyridine compounds to control, either by post-emergent or pre-emergent application, the growth of small seeded grasses and broadleaf plants, such as, for example, barnyard grass, crabgrass, yellow foxtail, Johnson grass, wild oats, bindweed, pigweed, ragweed and wild mustard. This ability is of the utmost importance since the compounds are not usually harmful to economical, large seeded crop plants, such as, for example, beans, corn, cotton, rice, soybeans or wheat. This feature allows for selective control of the undesirable small seeded plants in the presence of the economical large seeded crop plants.

The application of the compounds of the present invention to plants and plant parts and their habitats, gives rise to varying degrees of response depending upon the nature of the plant or seed, the stage of growth or maturity of the plant, the specific compound employed, and the dosage at which the exposure is carried out as well as environmental conditions. When large dosages of many of the compounds are applied to the foliage of undesirable plants, a substantially complete kill is obtained. Soil or foliar applications of more dilute dosages of many of the compounds suppress the growth of the germinant seeds and seedlings of many undesirable grasses while having little or no effect upon the seeds, emerging seedlings or established plants of many desirable crop plants. Thus, many of the pyridine compounds can be employed for the selective control of emerging seedlings of undesirable weeds in plantings or stands of desirable crop plants.

The minimum amount of active compound applied should be that which is effective in controlling and/or killing undesirable plant growth. Ordinarily, for pre-emergent control, good results are obtained when from 0.01 to 50 pounds or more of at least one of the active pyridine compounds are applied per acre. In foliage treatments, good results are obtained when from 0.5 to 200 pounds of active compound per acre are employed. In selective applications to foliage for the control of many undesirable weeds in the presence of desired crop plants, a uniform dosage of from about 1.0 to 75 pounds of active compound can be employed. In all selective applications, the exact dosage to be employed is dependent upon the resistance of the crop plant or their seeds to the pyridine compounds.

The present invention can be carried out by directly employing the pyridine compounds singly or in combination with each other. However, the present invention also embraces the employment of liquid, granular, encapsulated or dust compositions containing at least one of said compounds. In such usage, the compound or compounds can be modified with one or more of a plurality of chemically inert additaments or pesticidal materials including solvents or other liquid carriers, surface active dispersing agents or coarsely or finely divided inert solids. The augmented compositions are also adapted to be employed as concentrates and subsequently diluted with additional inert carrier, to produce other compositions in the form of dusts, sprays, granules, washes or drenches. In compositions where the additament is a coarsely or finely divided solid, a surface active agent or the combination of a surface active agent and a liquid additament, the added material cooperates with the active component so as to facilitate the invention. Whether the composition is employed in liquid form, as a wettable powder, or as a granular or encapsulated material, the active compound will normally be present in an amount of from about 5 to about 95 percent by weight of the total composition.

In the preparation of dust compositions, the toxicant products can be compounded with any of the finely divided solids, such as pyrophyllite, talc, chalk, gypsum, fuller's earth, bentonite, attapulgite, and the like. In such operations, the finely divided carrier is ground or mixed with the toxicant or wet with a solution of the toxicant in a volatile organic solvent. Also, such dust compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided attapulgite, bentonite, diatomite, or the like.

Similarly, the toxicant products can be compounded with a suitable water-immiscible organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of water-immiscible solvent, emulsifying agent and water. Preferred dispersing agents which can be employed in these compositions, are oil-soluble materials including non-ionic emulsifiers such as the condensation products of alkylene oxides with the inorganic acids, polyoxyethylene derivatives or sorbitan esters, complex ether alcohols and the like. Also, oil-soluble ionic emulsifying agents such as mahogany soaps can be used. Suitable organic liquids which can be employed in the composition include petroleum oils and distillates, toluene, liquid halohydrocarbons and synthetic organic oils. The surface-active dispersing agents are usually employed in liquid composition and in the amount of from 0.1 to 20 percent by weight of the combined weight of the dispersing agent and active compound.

In addition, other liquid compositions containing the desired amount of effective agent can be prepared by dissolving the toxicant in an organic liquid such as acetone, methylene chloride, chlorobenzene and petroleum distillates. The preferred organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F. at atmospheric pressure and having a flash point above 80° F. The proportion of the compounds of this invention employed in a suitable solvent may vary from about 2 to about 50 percent or higher.

In further embodiments, the compounds as employed in accordance with the present invention, or compositions containing the same, can be advantageously employed in the present invention in combination with one or more pesticidal or preservative compounds. In such embodiments, the pesticidal or preservative compound is employed either as a supplemental toxicant or as an additament. Representative operable pesticidal or preservative compounds include substituted phenols, cresols, substituted cresols and their metal salts, bisphenols and thiobisphenols; halogenated salicylanilides, organosulfur compounds, carbamate compounds, quaternary ammonium compounds, organometallic compounds, inorganic salts and miscellaneous other compounds, such as phenol, cresol, trichlorophenols, tetrachlorophenols, pentachlorophenol, p-chloro-m-cresol, sodium pentachlorophenol and other sodium, potassium, etc. salts of the phenols, substituted phenols, cresols and substituted cresols, di- and tribrominated salicylanilides, 2,2'-methylenebis-(3,4,6-trichlorophenol), 2,2'-thiobis(4,6-dichlorophenoxide), halogenated trifluoromethyl salicylanilide, disodium ethylenebisthiocarbamate, sodium N-methyldithiocarbamate, zinc dimethyldithiocarbamate, 2-mercaptobenzothiazole, 3,5-dimethyltetrahydro-1,3,5H-thiadiazine-2-thione, 2,3-dinitro-1,4-dithia-anthraquinone, dodecyl pyridinium chloride, alkyl dimethyl benzyl ammonium chloride, dialkyl dimethylammonium chloride, bistributyltin oxide, bis-tripropyltin oxide, copper pentachlorophenate, copper 8-hydroxyquinolate, sodium borate, 9-undecylenic acid, 10,10'-oxybisphenoxarsine, 1-(3-chloroallyl)-3,5,7-triaza-1-azoniaadamantane chloride, 1,4-bromobisacetobutene and substituted phosphorothioates (soil applied insecticides).

In application to an area to be treated, the compounds of this invention may be applied by spraying or by the use of mechanical spreaders in accordance with conventional practice. With respect to application, however, it will be noted that, depending upon the particular circumstances encountered, one method of application may be preferable over others. Thus, for example, for preferred pre-emergence application it has been found very satisfactory to apply the active compound in a liquid spray or on granules and incorporate it into the soil.

In a further method, the distribution can be accomplished by introducing a toxicant or toxicants into the water employed to irrigate the soil. In this method, the amount of water or field capacity of the soil in order to obtain the desired depth of distribution of the toxicant.

The following embodiments are illustrative of the present methods.

EXAMPLE VI:

Forty-five parts by weight of 4-dibutylamino-3,5-difluoro-2-(2-hydroxethoxy)pyridine is mixed and ground with 5 parts by weight of Triton X-155 surfactant (an alkylated aryl polyether alcohol) to prepare a water-dispersible concentrate composition containing 90 percent by weight of the pyridine compound.

In a further operation, 25 parts by weight of 6-amino-3,5-dichloro-2-[(2-butylthio)-1-methylethoxy]pyridine, 10 parts by weight of Triton X-155 surfactant and 65 parts by weight of xylene are mixed together to prepare an emulsifiable concentrate composition containing 25 percent by weight of said compound.

A mixture of 10 parts by weight of 3,5-dibromo-6-methylamino-2-(2-butoxyethoxy)pyridine, 10 parts by weight 3,5-dibromo-4-methylamino-2-(2-dimethylamino-1-methylethoxy)pyridine, 0.1 part of Nacconol NR detergent (alkyl sulfonate), 0.1 part of Daxad No. 27 (a polymerized sodium salt of benzoid alkyl sulfonic acids) and 200 parts of water are ball-milled together to prepare a water dispersible liquid concentrate composition containing 20 parts by weight of the mixed pyridine compounds. The concentrate compositions thus prepared can be dispersed in water to prepare aqueous compositions which have very desirable wetting and penetrating properties and are adapted to distribute growth inhibiting amounts of the pyridine compound on plant parts.

EXAMPLE VII

In separate operations, aqueous compositions containing pyridine compounds are prepared as follows:

4 parts by weight of one of the pyridine compounds, 0.08 part of sorbitan trioleate (Span 85), and 0.02 part of a sorbitan monoleate polyoxyethylene derivative (Tween 80) are dispersed in 40 milliliters of acetone to produce a concentrate composition in the form of a water-soluble liquid containing one of the pyridine compounds as the sole active agent. The compounds employed in these procedures include the following:

3,5-difluoro-2-[2-(hydroxymethoxy)ethoxy]-6-dipropylamino pyridine;
3,5-dichloro-2-(2-hydroxyethoxy)-4-n-propylamino pyridine; hydrobromide;
4-anilino-3,5-dichloro-6-fluoro-2-(2-hydroxy-1-methylethoxy)pyridine;
4-amino-3,5-dichloro-2-[2-(benzyloxy)ethoxy]pyridine;
4-acetamido-3,5-dichloro-2-(2-hydroxyethoxy)pyridine;
4-(benzylamino)-3,5-dichloro-2-(2-hydroxyethoxy)-pyridine;
3,5,6-trifluoro-2-[1-methyl-2-(phenylbutoxy)ethoxy]-4-[(4-phenylbutyl)amino]pyridine;
3,5-dichloro-2-(2-hydroxyethoxy)-4-n-propylamino pyridine;
3,5-dichloro-2-(2-hydroxyethoxy)-4-n-propylamino pyridine, sulfuric acid salt;
4-amino-3,5-dibromo-2-(2-hydroxyethoxy)pyridine;
3,5-dichloro-2-[2-(2,2-dichlorobutyroyloxy)ethoxy]-6-dimethylamino pyridine;
3,5-difluoro-4-dimethylamino-2-(2-hydroxyethoxy)-pyridine;
3,5-difluoro-4-dmethylamino-2-(2-hydroxyethoxy)-pyridine, sulfuric acid salt;
4-amino-3,5-dichloro-2-(6-hydroxyhexoxy)pyridine;
3,5-dibromo-2-(2-butoxyethoxy)-6-methylamino pyridine;
3,5-dibromo-4-diethylamino-2-[2-(butyroyloxy)ethoxy]-pyridine;
3,5-dibromo-4-methylamino-2-[2-(dimethylamino)-1-methylethoxy]pyridine;
4-amino-3,5,6-trichloro-2-(2-hydroxyethoxy)pyridine;
3,5-dibromo-4-diethylamino-2-[2-(4-hydroxybutoxy)-1-methylethoxy]pyridine;
6-butylamino-3,5-difluoro-2-(2-hydroxyethoxy)-pyridine;
4-amino-3,5-dichloro-2-(3-ethoxy-2-hydroxypropoxy)-pyridine;
4-amino-3,5-dichloro-2-(6-hydroxyhexoxy)pyridine, dichloroacetic acid salt;
2-(2-anilinoethoxy)-3,5-dibromo-4-butyramido-6-fluoropyridine;
4-(N-butyl butyramido)-3,5,6-trichloro-2-(2-phenoxyethoxy)pyridine;
4-amino-3,5-dichloro-2-(2-acetoxyethoxy)pyridine;
4-acetamido-3,5-dichloro-2-(2-hydroxyethoxy)pyridine;
4-acetamido-3,5-dichloro-2-(2-acetoxyethoxy)pyridine;
4-(N-methyl acetamido)-3,5-dichloro-6-fluoro-2-(2-hydroxyethoxy)pyridine;
3,5-difluoro-4-dimethylamino-2-(2-hydroxyethoxy)-pyridine, sulfuric acid salt;
6-amino-3,5-dichloro-2-(2-chloroacetoxyethoxy)-pyridine;
6-amino-3,5-dichloro-2-(2-trichloroacetoxy-1-methylethoxy)pyridine;
6-amino-3,5-dichloro-2-(2-hydroxyethoxy)pyridine, hydroiodide;
4-dibutyl-3,5-difluoro-2-(2-hydroxyethoxy)pyridine, 2,2-dichloropropionic acid salt;
6-amino-3,5-difluoro-2-(2-mercaptoethoxy)pyridine;
6-amino-3,5-dichloro-2-[2-(butylthio)-1-methylethoxy]-pyridine;
4-dibutylamino-3,5-difluoro-2-(2-hydroxyethoxy)-pyridine;
4-amino-3,5-dichloro-2-[2-(2-propenoxy)ethoxy]-pyridine;
4-amino-3,5-dichloro-2-butoxy pyridine;
6-amino-3,5-difluoro-2-(2-mercaptoethoxy)pyridine, trichloroacetic acid salt;
4-amino-3,5,6-trichloro-2-(2-ethoxy-1-methylethoxy)-pyridine.

Portions of these concentrate compositions are dispersed in separate portions of water to provide aqueous compositions, each containing 0.44 pound of one of the pyridine compounds per 100 gallons of ultimate aqueous mixture. The diluted compositions have very desirable wetting and penetrating properties and are adapted to distribute growth inhibiting amounts of the pyridine compound on plant parts.

EXAMPLE VIII

Representative products of the present invention were evaluated for the control of barnyard grass. In these evaluations, plots of barnyard grass of a height of about 4 inches were used. Aqueous spray compositions, each containing 4,000 parts of a given pyridine compound per million parts of ultimate composition, were prepared in accordance with the procedures of Example VI, and each separate composition was applied to a separate plot. The application was made to the point of run-off and was carried out with conventional spraying equipment. Other plots were sprayed with a similar composition containing no toxicant to serve as controls. Thereafter, the plots were maintained under conditions conducive for plant growth. Two weeks after treatment, the plots were examined for plant growth and evaluated. The results of the examination of the treated plots are set forth in the following table.

TABLE A

| Compound | Percent Kill and Control of Barnyard Grass |
|---|---|
| 4-amino-3,5-dichloro-2-(2-hydroxyethoxy)pyridine | 100 |
| 4-amino-3,5-dichloro-2-(2-hydroxyethoxy)pyridine, hydrochloride | 95 |
| 4-amino-3,5,6-trichloro-2-(2-hydroxyethoxy)pyridine | 90 |
| 4-amino-3,5-dichloro-2-(2-hydroxy-1-methylethoxy)pyridine | 90 |
| 3,5-dichloro-4-methylamino-2-(2-hydroxyethoxy)pyridine | 95 |
| 4-amino-3,5-dichloro-2-(2-acetoxyethoxy)pyridine | 90 |
| 4-amino-3,5-dichloro-2-[2-(benzyloxy)ethoxy]pyridine | 80 |
| 4-amino-3,5-dichloro-2-(4-hydroxybutoxy)pyridine | 90 |
| 4-amino-2-(2-aminoethoxy)-3,5-dichloropyridine | 90 |
| 4-amino-3,5-dichloro-2-(2-methoxyethoxy)pyridine | 80 |
| Control | 0 |

EXAMPLE IX

In another representative operation, representative products were evaluated for the control of yellow foxtail employing the dosage rate and procedures as set forth in Example VII. The results of the examination are set forth in the following table.

TABLE B

| Compound | Percent Kill and Control of Yellow Foxtail |
|---|---|
| 4-amino-3,5-dichloro-2-(2-hydroxyethoxy)pyridine | 90 |
| 4-amino-3,5-dichloro-2-(2-hydroxyethoxy)pyridine, hydrochloride | 95 |
| 4-amino-3,5-dichloro-2-(2-hydroxy-1-methylethoxy)-pyridine | 95 |
| 3,5-dichloro-4-methylamino-2-(2-hydroxyethoxy)pyridine | 90 |
| 4-amino-3,5-dichloro-2-(4-hydroxybutoxy)pyridine | 95 |
| 3,5-dichloro-4-dimethylamino-2-(2-hydroxyethoxy)pyridine | 90 |
| 4-amino-3,5,6-trichloro-2-(2-hydroxyethoxy)pyridine | 90 |
| 4-amino-3,5,6-trichloro-2-(2-ethoxy-1-methylethoxy)-pyridine | 90 |
| 3,5-dichloro-2-(2-hydroxyethoxy)-4-n-propylamino pyridine | 85 |
| 4-amino-3,5-dichloro-2-(2-acetoxyethoxy)pyridine | 90 |
| 4-amino-3,5-dichloro-2-butoxy pyridine | 95 |
| 4-amino-3,5-dichloro-2-[2-(benzyloxy)ethoxy]pyridine | 85 |
| 4-(benzylamino)-3,5-dichloro-2-(2-hydroxyethoxy)pyridine | 80 |
| 4-amino-2-(2-aminoethoxy)-3,5-dichloro pyridine | 90 |
| 4-amino-3,5-dichloro-2-(2-methoxyethoxy)pyridine | 95 |
| Control | 0 |

EXAMPLE X

Aqueous compositions of various pyridine compounds prepared in accordance with Example VI were employed for pre-emergent applications on plots immediately after they were seeded with crabgrass. Other plots similarly seeded were treated with like compositions containing no toxicant to serve as control plots. The treating applications were carried out by drenching the soil with the aqueous compositions to obtain a treating rate of 20 pounds per acre. Thereafter, the plots were maintained under conditions conducive for good plant growth. Two weeks after treatment, the plots were examined to determine the percent kill and control of crabgrass. The results of the examinations are set forth in the following table.

TABLE C

| Compound | Percent Kill and Control of Crabgrass |
|---|---|
| 6-amino-3,5-dichloro-2-(2-hydroxyethoxy)pyridine | 100 |
| 4-amino-3,5-dichloro-2-[2-(2-hydroxyethoxy)ethoxy]pyridine | 100 |
| 3,5,6-trichloro-2-(2-hydroxyethoxy)-4-methylamino pyridine | 100 |
| 4-amino-3,5,6-trichloro-2-(2-ethoxy-1-methylethoxy)pyridine | 100 |
| 4-amino-3,5-dichloro-2-(2-hydroxyethoxy)pyridine | 100 |
| 4-amino-3,5-dichloro-2-(2-hydroxyethoxy)pyridine, hydrochloride | 100 |
| 4-(benzylamino)-3,5-dichloro-2-(2-hydroxyethoxy)pyridine | 100 |
| 4-amino-3,5-dichloro-2-[2-(benzyloxy)ethoxy]pyridine | 100 |
| 4-amino-3,5-dichloro-2-(2-acetoxyethoxy)pyridine | 100 |
| 4-acetamido-3,5-dichloro-2-(2-acetoxyethoxy)pyridine | 100 |
| 4-amino-3,5-dichloro-2-(2-hydroxy-1-methylethoxy)pyridine | 100 |
| 4-amino-3,5-dichloro-2-(4-hydroxybutoxy)pyridine | 100 |
| 3,5-dichloro-4-methylamino-2-(2-hydroxyethoxy)pyridine | 100 |
| 4-amino-3,5-dichloro-2-butoxy pyridine | 100 |
| Control | 0 |

EXAMPLE XI

Aqueous solutions prepared in accordance with Example VI and containing representative pyridine compounds, were employed for pre-emergent applications on plots immediately after they were seeded with barnyard grass, yellow foxtail, wild mustard, bindweed and pigweed. Other plots similarly seeded with the named plant species were treated with compositions containing none of the toxicant. The treating applications were carried out by drenching the soil with the aqueous solutions to obtain a treating rate of 20 pounds per acre.

Thereafter, the plots were maintained under conditions conducive for plant growth. After a two-week period, the plots were examined to determine the percent kill and control of the named plant species. The results of the examinations are set forth in the following table.

complete kill and control of barnyard grass, Johnson grass, bindweed, pigweed and wild mustard and profuse growth of wheat. In the control plots, no kill or control of any of the plant species could be seen.

TABLE D

| Compound Employed | Percent Kill and Control of | | | | |
|---|---|---|---|---|---|
| | Wild Mustard | Barnyard Grass | Yellow Foxtail | Bindweed | Pigweed |
| 4-amino-3,5-dichloro-2-(2-hydroxyethoxy)pyridine | 100 | 100 | 100 | 100 | 100 |
| 4-amino-3,5-dichloro-2-(2-hydroxyethoxy)pyridine, hydrochloride | 100 | 100 | 100 | 100 | 100 |
| 4-amino-3,5-dichloro-2-[2-(2-hydroxyethoxy)ethoxy]pyridine | 100 | — | 80 | 100 | 100 |
| 4-amino-3,5-dichloro-2-(2-hydroxy-1-methylethoxy)pyridine | 100 | 100 | 100 | 100 | 100 |
| 3,5-dichloro-2-(2-hydroxyethoxy)-4-methylamino pyridine | 100 | 100 | 100 | 100 | 100 |
| 4-amino-3,5-dichloro-2-(4-hydroxybutoxy)pyridine | 100 | 95 | 100 | 100 | |
| 4-dimethylamino pyridine 3,5-dichloro-2-(2-hydroxyethoxy)-4-dimethylamino pyridine | 100 | 90 | 100 | 100 | 100 |
| 3,5-dichloro-2-(2-hydroxyethoxy)-4-propylamino pyridine | 100 | 100 | 100 | 100 | 100 |
| 3,5,6-trichloro-2-(2-hydroxyethoxy)-4-methylamino pyridine | 100 | 75 | 100 | 100 | 100 |
| 4-amino-3,5,6-trichloro-2-(2-ethoxy-1-methylethoxy)pyridine | 100 | 100 | 100 | 100 | 100 |
| 4-amino-3,5-dichloro-2-butoxy pyridine | 100 | 90 | 100 | 80 | 100 |
| 4-acetamido-3,5-dichloro-2-(2-acetoxyethoxy)pyridine | 100 | 80 | 100 | 95 | 100 |
| 4-amino-3,5-dichloro-2-(2-acetoxyethoxy)pyridine | 100 | 100 | 100 | 100 | 100 |
| 4-(benzylamino)-3,5-dichloro-2-(2-hydroxyethoxy)pyridine | 100 | 90 | 70 | 100 | 100 |
| 4-amino-3,5-dichloro-2-[2-(benzyloxy)-ethoxy]pyridine | 75 | — | 100 | 80 | 100 |
| 4-amino-2-(2-aminoethoxy)-3,5-dichloropyridine | 100 | 95 | 100 | 100 | 100 |
| 6-amino-3,5-dichloro-2-(2-hydroxyethoxy)pyridine | 100 | 100 | 100 | 100 | 100 |
| 4-amino-3,5-dichloro-2-(2-methoxyethoxy)pyridine | 100 | 85 | 100 | 100 | 100 |
| 3,5-dichloro-2-(2-hydroxyethoxy)-6-dimethylamino pyridine | 100 | 90 | 80 | 100 | 100 |
| Control | 0 | 0 | 0 | 0 | 0 |

EXAMPLE XII

4-Amino-2-(2-aminoethoxy)-3,5-dichloro pyridine was employed for the selective control of emerging seedlings of the small seeded plants, barnyard grass, yellow foxtail, Johnson grass, bindweed, pigweed, ragweed and wild mustard in plots seeded with the above-named plant species and the large seeded crop plant soybeans. The plots were treated with aqueous compositions prepared as set forth in Example VI containing the above-named compound as the sole toxicant therein. Other plots similarly seeded with the above-named plant species were treated with aqueous compositions containing no toxicant to serve as control plots. The treating applications were carried out by drenching the soil with the aqueous compositions to obtain a treating rate of 2 pounds per acre. Thereafter, the plots were maintained under conditions conducive to good plant growth. Examination of the plots two weeks after treatment showed substantially complete kill and control of all of the small seeded plant species and profuse growth of soybeans. In the control plots, no kill or control of any of the plant species could be ascertained.

EXAMPLE XIII 3,5-Dichloro-2-(2-hydroxyethoxy)-4-dimethylamino pyridine was employed for the selective control of emerging seedlings of barnyard grass, Johnson grass, bindweed, pigweed and wild mustard in plots seeded with both the above-named species and the crop plant wheat. The operations were carried out in accordance with the procedures recorded in Example X. Examination two weeks after treatment showed substantially

EXAMPLE XIV 3,5,6-Trichloro-2-(2-hydroxyethoxy)-4methylamino pyridine and 4-amino-3,5,6-trichloro-2-(2-hydroxyethoxy)-pyridine were evaluated for the selective pre-emergent control of bindweed in plots seeded with this plant and soybeans. The operations were carried out in accordance with the procedures recorded in Example X. Examination two weeks after treatment showed substantially complete kill and control of bindweed and profuse growth of soybeans. In the control plots, no kill or control of any of the plant species could be seen.

EXAMPLE XV 3,5-Dichloro-2-(2-hydroxyethoxy)-4-dimethylamino pyridine and 4-amino-2-(2-aminoethoxy)-3,5-dichloro pyridine were evaluated for the selective post-emergent control of barnyard grass and yellow foxtail in plots containing these plant species and cotton plants. In these evaluations, the plants were of a height of about 4 inches. Aqueous spray compositions, each containing 1000 parts of one of the compounds per million parts of ultimate composition and prepared in accordance with the procedures of Example X, were separately applied to the plots so that each plot was treated with a different composition. The application was made to the point of run-off employing conventional spraying equipment. Other plots containing the same plant species were treated with compositions containing no toxicant, to serve as controls. Thereafter, the plots were held for a period of two weeks under conditions conducive for good plant growth. At the end of this period, the plots were examined to determine the degree of kill and control of the plants. In the control plots, all of the plants were growing rapidly and no kill or control of any of the plants could be found. In the treated plots, there was substantially complete kill and control of both barnyard grass and yellow foxtail and no injury could be found to the cotton plants which were thriving and growing profusely.

PREPARATION OF STARTING MATERIALS

The 4- and 6-amino trihalo- or tetrahalopyridines employed as starting materials can be prepared by treating an appropriate tetrahalo- or pentahalopyridine at a temperature of about 160°–200° C. with aqueous ammonia.

The 4- and 6-monoloweralkylamino trihalo- or tetrahalopyridines employed as starting materials can be prepared by reacting a monoloweralkylamine with an appropriate 4- or 6-methylsulfonyl-, trihalo- or tetrahalopyridine at a temperature of from about 15° C. to about 60° C. in the presence of a solvent such as dimethylformamide.

The 4- and 6-diloweralkylamino trihalo- or tetrahalopyridines employed as starting materials can be prepared by reacting an aqueous appropriate diloweralkylamine with an appropriate tetrahalo- or pentahalopyridine at temperatures of from about 100° C. to about 175° C. and at a pressure of from atmospheric to about 75 pounds per square inch.

What is claimed is:

1. A compound corresponding to the formula

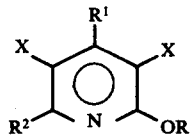

and the organic or inorganic acid addition salts thereof, wherein X represents chloro, bromo or fluoro; $R^1$ represents hydrogen, amino, loweralkylamino, arylamino from the group consisting of phenylamine, benzylamine, phenylethylamine, phenylpropylamine and phenylbutylamine, loweralkylamido or N-(loweralkyl)-loweralkylamido; $R^2$ represents hydrogen, X, amino or loweralkylamino; with the proviso that one of $R^1$ or $R^2$ is always amino or loweralkylamino and the other of $R^1$ or $R^2$ is other than amino or loweralkylamino; R represents butyl, 2-hydroxypropyl, 4-hydroxybutyl, 6-hydroxyhexyl or the radical

wherein Z represents amino, loweralkylamino, phenylamino, hydroxy, loweralkoxy, aryloxy from the group consisting of phenyloxy, benzyloxy, phenylethoxy, phenylpropoxy and phenylbutoxy, 2-propenyl, hydroxyloweralkoxy, mercapto, loweralkylthio, loweralkanoyloxy or 2-haloloweralkanoyloxy and $R^3$ represents hydrogen or methyl and with the proviso that R is other than butyl when $R^2$ is X.

2. The compound of claim 1 wherein $R^1$ is hydrogen.
3. The compound of claim 1 wherein $R^2$ is hydrogen.
4. The compound of claim 3 which is 4-amino-3,5-dichloro-2-(2-hydroxyethoxy)pyridine.
5. The compound of claim 3 which is 4-amino-3,5-dichloro-2-(2-hydroxy-1-methylethoxy)pyridine.
6. The compound of claim 3 which is 3,5-dichloro-2-(2-hydroxyethoxy)-4-dimethylamino pyridine.
7. The compound of claim 1 which is 3,5,6-trichloro-2-(2-hydroxyethoxy)-4-methylamino pyridine.
8. The compound of claim 1 which is 4-amino-3,5,6-trichloro-2-(2-hydroxyethoxy)pyridine.
9. The compound of claim 1 which is 4-amino-3,5,6-trichloro-2-(2-ethoxy-1-methylethoxy)pyridine.
10. The compound of claim 1 wherein the compound is an acid addition salt of one of hydrochloric acid, hydrobromic acid, hydroiodic acid, sulfuric acid, phosphoric acid, nitric acid, dichloroacetic acid, trichloroacetic acid or 2,2-dichloropropionic acid.
11. The compound of claim 10 which is 4-amino-3,5-dichloro-2-(2-hydroxyethoxy)pyridine, hydrochloride.
12. A method for controlling the growth of undesirable plant species which comprises applying to plants, plant parts or their habitats a growth inhibiting amount of at least one pyridine compound corresponding to the formula

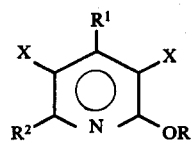

and the organic or inorganic acid addition salts thereof, wherein X represents chloro, bromo or fluoro; $R^1$ represents hydrogen, amino, loweralkylamino, arylamino from the group consisting of phenylamine, benzylamine, phenylethylamine, phenylpropylamine and phenylbutylamine, loweralkylamido or N-(loweralkyl)-loweralkylamido; $R^2$ represents hydrogen, X, amino or loweralkylamino; with the proviso that one of $R^1$ or $R^2$ is always amino or loweralkylamino and the other of $R^1$ or $R^2$ is other than amino or loweralkylamino; R represents butyl, 2-hydroxypropyl, 4-hydroxybutyl, 6-hydroxyhexyl or the radical

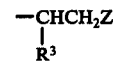

wherein Z represents amino, loweralkylamino, phenylamino, hydroxy, loweralkoxy, aryloxy from the group consisting of phenyloxy, benzyloxy, phenylethoxy, phenylpropoxy and phenylbutoxy, 2-propenyl, hydroxyloweralkoxy, mercapto, loweralkylthio, loweralkanoyloxy or 2-haloloweralkanoyloxy and $R^3$ represents hydrogen or methyl and with the proviso that R is other than butyl when $R^2$ is X.

13. The method of claim 12 wherein the pyridine compound is 4-amino-3,5-dichloro-2-(2-hydroxyethoxy)pyridine.
14. The method of claim 12 wherein the pyridine compound is 4-amino-3,5-dichloro-2-(2-hydroxy-1-methylethoxy)pyridine.
15. The method of claim 12 wherein the pyridine compound is 3,5-dichloro-2-(2-hydroxyethoxy)-4-dimethylamino pyridine.
16. The method of claim 12 wherein the compound is an acid addition salt of one of hydrochloric acid, hydrobromic acid, hydroiodic acid, sulfuric acid, phosphoric acid, nitric acid, dichloroacetic acid, trichloracetic acid or 2,2-dichloropropionic acid.

17. The method of claim 16 which is 4-amino-3,5-dichloro-2-(2-hydroxyethoxy)pyridine, hydrochloride.

18. The method of claim 12 wherein the pyridine compound is applied pre-emergent.

19. The method of claim 12 wherein the pyridine compound is applied post-emergent.

20. A composition for the control of undesirable plant growth which comprises as the active agent a compound corresponding to the formula

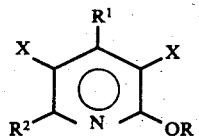

and the organic or inorganic acid addition salts thereof, wherein X represents chloro, bromo or fluoro; $R^1$ represents hydrogen, amino, loweralkylamino, arylamino from the group consisting of phenylamine, benzylamine, phenylethylamine, phenylpropylamine and phenylbutylamine, loweralkylamido, or N-(loweralkyl)-loweralkylamido; $R^2$ represents hydrogen, X, amino or loweralkylamino; with the proviso that one of $R^1$ or $R^2$ is always amino or loweralkylamino and the other of $R^1$ or $R^2$ is other than amino or loweralkylamino; R represents loweralkyl, 2-hydroxypropyl, 4-hydroxybutyl, 6-hydroxyhexyl or the radical

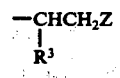

wherein Z represents amino, loweralkylamino, phenylamino, hydroxy, loweralkoxy, aryloxy from the group consisting of phenyloxy, benzyloxy, phenylethoxy, phenylpropoxy and phenylbutoxy, 2-propenyl, hydroxyloweralkoxy, mercapto, loweralkylthio, loweralkanoyloxy or 2-haloloweralkanoyloxy and $R^3$ represents hydrogen or methyl and with the proviso that R is other than butyl when $R^2$ is X in an amount sufficient to inhibit said plant growth and in admixture with a chemically inert solid or liquid carrier therefor.

21. The composition of claim 20 wherein the active agent constitutes from about 5 to about 95 percent by weight of the total composition.

* * * * *

UNITED STATES PATENT AND TRADEMARK OFFICE
CERTIFICATE OF CORRECTION

PATENT NO. : 4,066,438

DATED : January 3, 1978

INVENTOR(S) : Howard Johnston and Herman O. Senkbeil

It is certified that error appears in the above-identified patent and that said Letters Patent are hereby corrected as shown below:

Column 1, line 35, "arkaryl," should read -- alkaryl, --.

Column 3, line 68, "cloroform" should read -- chloroform --.

Column 7, line 59, "2-[2-dimethylamino)-1-" should read -- 2-[2-(dimethylamino)-1- --.

Column 10, line 59, "-1,3,5H-thiadiazine-" should read -- -1,3,5-2H-thiadiazine- --.

Column 11, line 15, after the words "amount of water" insert the omitted statement -- can be varied in accordance with the moisture equivalent --.

Column 11, line 22, "difluoro-2-(2-hydroxethoxy)pyridine" should read -- difluoro-2-(2-hydroxyethoxy)pyridine --.

Column 12, line 14, "3,5-difluoro-4-dmethylamino-2-(2-" etc. should read -- 3,5-difluoro-4-dimethylamino-2-(2- --.

Columns 15 and 16, TABLE D, subcolumn "Pigweed", the blank space between the 5th and 7th "100" should read -- 100 --.

Columns 15 and 16, TABLE D, column "Compound Employed", the 12th line, "4-dimethylamino pyridine" should be deleted.

Column 16, line 38, "3,5,6-Trichloro-2-(2-hydroxyethoxy)--4methylamino" should read -- 3,5,6-Trichloro-2-(2-hydroxyethoxy)-4-methylamino --.

UNITED STATES PATENT AND TRADEMARK OFFICE
CERTIFICATE OF CORRECTION CONTINUED

PATENT NO. : 4,066,438  
DATED : January 3, 1978  
INVENTOR(S) : Howard Johnston and Herman O. Senkbeil Page 2 of 2

It is certified that error appears in the above-identified patent and that said Letters Patent are hereby corrected as shown below:

Column 19, line 1, "trichloracetic acid" should read -- trichloroacetic acid --.

Signed and Sealed this

Eighteenth Day of April 1978

[SEAL]

Attest:

RUTH C. MASON  
*Attesting Officer*

LUTRELLE F. PARKER  
*Acting Commissioner of Patents and Trademarks*